United States Patent
Ubukata et al.

(10) Patent No.: US 10,563,159 B2
(45) Date of Patent: Feb. 18, 2020

(54) CELL-HOLDING CONTAINER AND CELL CULTURE METHOD USING SAME

(71) Applicant: ASAHI RUBBER INC., Saitama-shi, Saitama (JP)

(72) Inventors: Yuya Ubukata, Saitama (JP); Tsutomu Takano, Saitama (JP); Kenichi Kagawa, Tokyo (JP); Shigenori Ozaki, Nirasaki (JP); Yusuke Yoda, Tokyo (JP); Tomoaki Kurakazu, Stevenage (GB)

(73) Assignee: ASAHI RUBBER INC., Saitama-shi (JP)

( * ) Notice: Subject to any disclaimer, the term of this patent is extended or adjusted under 35 U.S.C. 154(b) by 0 days.

(21) Appl. No.: 15/742,679

(22) PCT Filed: Jul. 5, 2016

(86) PCT No.: PCT/JP2016/069940
§ 371 (c)(1),
(2) Date: Jan. 8, 2018

(87) PCT Pub. No.: WO2017/006942
PCT Pub. Date: Jan. 12, 2017

(65) Prior Publication Data
US 2018/0201891 A1    Jul. 19, 2018

(30) Foreign Application Priority Data
Jul. 6, 2015  (JP) .................. 2015-135506

(51) Int. Cl.
*C12M 1/00* (2006.01)
*C12M 1/32* (2006.01)

(52) U.S. Cl.
CPC ............ *C12M 23/26* (2013.01); *C12M 23/12* (2013.01); *C12M 23/22* (2013.01)

(58) Field of Classification Search
CPC .............................. C12M 23/26; C12M 23/12
See application file for complete search history.

(56) References Cited

U.S. PATENT DOCUMENTS

| 6,022,921 A | * | 2/2000 | Achenbach | C08J 7/065 |
| | | | | 524/108 |
| 6,048,723 A | * | 4/2000 | Banes | C12M 23/12 |
| | | | | 435/288.3 |

(Continued)

FOREIGN PATENT DOCUMENTS

| JP | S61-242576 A | 10/1986 |
| JP | 2005-534001 A | 11/2005 |

(Continued)

OTHER PUBLICATIONS

Sep. 27, 2016 International Search Report issued in International Patent Application No. PCT/JP2016/069940.

(Continued)

*Primary Examiner* — Kara D Johnson
(74) *Attorney, Agent, or Firm* — Oliff PLC

(57) ABSTRACT

A cell-holding container comprises: an elastic body for holding cells including at least any one of adherent cells at least one selected from the group consisting of stem cells, progenitor cells, somatic cells and germ cells, and suspended cells at least one selected from the group consisting of blood cells, T cells and B cells; and the elastic body is formed of a rubber material containing a rubber component including an additional crosslinking silicone rubber and is able to hold the cells.

14 Claims, 7 Drawing Sheets

(56) References Cited

U.S. PATENT DOCUMENTS

| | | |
|---|---|---|
| 2005/0232916 A1 | 10/2005 | Martin et al. |
| 2006/0019376 A1 | 1/2006 | Bungay et al. |
| 2006/0293724 A1 | 12/2006 | Kronberg et al. |
| 2012/0135513 A1 | 5/2012 | Muller-Rees et al. |

FOREIGN PATENT DOCUMENTS

| | | |
|---|---|---|
| JP | 2009-198909 A | 9/2009 |
| JP | 2011-036221 A | 2/2011 |
| JP | 2013-247943 A | 12/2013 |
| JP | 2014-018185 A | 2/2014 |
| JP | 2014-176463 A | 9/2014 |
| JP | 2015-116150 A | 6/2015 |
| WO | 2015/033824 A1 | 3/2015 |
| WO | 2015/105029 A1 | 7/2015 |

OTHER PUBLICATIONS

Jul. 13, 2017 Office Action issued in Japanese Patent Application No. 2017-527471.
Sep. 27, 2016 Written Opinion issued in International Patent Application No. PCT/JP2016/069940.
Nov. 6, 2018 European Search Report issued in European Application No. 168214112.

\* cited by examiner

CELL-HOLDING CONTAINER AND CELL CULTURE METHOD USING SAME

TECHNICAL FIELD

The present invention relates to a cell-holding container for culturing and forming cell clusters by aggregating induced pluripotent stem cells (iPS cells) and embryonic stem cells (ES cells) on an elastic body formed of a rubber material, and a cell culture method using the same.

BACKGROUND OF THE ART

A subculture of various cells such as adherent cells and suspended cells has been conventionally conducted. For example, cells which are adhering to a culturing container and proliferated, are released therefrom by a physical method using a cell scraper or a pipette, or a physiological method using an enzyme, and then the cells are seeded in a new culturing container having a fresh culture medium and conducted with subculture. Especially, because pluripotent stem cells which are the adherent cells easily result in cell death when purifying into single cells, it is necessary to conduct the subculture while maintaining cell masses. For instance, the pluripotent stem cells are released as colonies, and the cell masses having appropriate size are disrupted by using a pipette etc., and then seeding it into a new culturing container to conduct the subculture thereof.

In the subculture, when a releasing means as the physical method is used, problems that the cells are excessively damaged are occurred. When the other releasing as the physiological method is used, the cells are damaged. Although this damage is smaller than that occurring from the physical method, the physiological method causes problems in which an enzyme reaction with respect to the cells is non-uniform and the cells are dead after differentiation into the single cells. Further, when the pipetting procedure is conducted, the size of the cell masses is varied and the cell masses having a uniform size is difficulty obtained. Thereby size of the colonies which is produced after the subculture is dispersed. According to the problems of the dispersion of the size of the respective colonies, even when the some colonies reach a specific size, an insufficient culture state of the culture of others is occurred. The dispersion of the size thereof adversely affects quality control of the cells and causes decrease of productive efficiency.

A method improving damage of the cells by the releasing means and non-uniformity of the colonies in the subculture is disclosed in Patent Document 1. Patent Document 1 discloses a substrate for holding or amplifying and culturing pluripotent stem cells, which includes a nanofiber consisting of a biopolymer, and a culturing method using the same. According to using the substrate, the pluripotent stem cells may be dispersed to the single cells by slight handling by the pipetting procedure without an enzyme treatment when conducting the subculture. Uniformed cells may be obtained while decreasing a cell death rate.

In addition, the pluripotent stem cells are easily differentiated. The pluripotent stem cells, which initiate differentiation, difficultly restore to a state of undifferentiation. A maintenance culture therefore needs to be conducted without changing to state which easily differentiates the cells. Further, when the differentiation of the cells is initiated while culturing it, it is necessary to remove the cells which initiate the differentiation from the culturing container because the other cells of circumference thereof are adversely affected, and a yield and purity of the undifferentiated cells are decreased.

In order to culture the cells, an opened-system culture and a closed-system culture have been used. According to the conventional opened-system culture using dishes, work of medium replacement of culture is carried out while opening a cover of the dishes. Therefore the cells which initiate the differentiation may be aspirated and removed by inserting an aspirator or a micropipette thereinto. The opened-system culture is inexpensive and has excellent operability and thus, it is useful for research.

On the other hand, according to the closed-system culture, because the aspirator cannot be inserted thereinto, it is difficult to selectively remove the cells which initiate the differentiation. In contrast, according to the closed-system culture, an incidence of contamination and infection risk may decrease than that of the opened-system culture. Therefore the closed-system culture is useful for medical care. Technology and structure of the closed-system culture, which is capable of selectively removing the cells initiating the differentiation by simple work, have been demanded.

As a method which is capable of selectively removing and recovering the cells in the closed-system culture, for example, a method for regionally and selectively releasing the cells from an adhesive face by high frequency vibration is disclosed in Patent Document 2. According to the method, the cells may be selectively released from an adhering face of the culturing container of the closed-system or the opened-system through a non-contact means.

Regardless of the closed-system culture and the opened-system culture, according to a cell culture method and a subculture using a container such as a multi plate of which wells as concave having a dented concave part for forming the cell clusters are molded therein, the container having excellent visibility is required in order to observe the cells in the wells. The cell culture method comprises introducing cell suspension which disperses the cells for culturing into the container; seeding the cells which are precipitated in the wells; forming the cell clusters and culturing them; and recovering the cultured cells by the handling using the pipette, by the high frequency vibration or by sending a cell-releasing solution as needed. The subculture may be carried out by repeating these steps.

The shape fixed container in which the wells are preliminarily molded has a problem of difficult observation, because visibility is insufficient due to a concave-convex shape of the container. When the cell suspension is introduced into the container, air bubble is easily mixed thereinto. The visibility therefore is further decreased, because an establishing position of the cell becomes an unstable state by existence both of the cells and the air bubble in the wells, and air bubble varies transmittance and a refractive index of light.

As described above, the various subcultures have been conventionally conducted. It have been demanded that a container and cell culture method using the same, which can solve the above problems, can culture the pluripotent stem cells of huge amount while maintaining the undifferentiated state thereof, can conduct observation and examination of a state of the cells from the outside direction of the container, and can perform a homogeneous subculture with more excellent efficiency.

PRIOR ART DOCUMENT

[Patent Document]
[Patent Document 1] Japanese Patent Application Publication No. 2013-247943
[Patent Document 2] Japanese Patent Application Publication No. 2014-018185

SUMMARY OF THE INVENTION

Problems to be Solved by the Invention

The present invention was made in view of solving the above described problems, and its object is to provide a cell-holding container in which cell clusters can be formed and cultured on an elastic body formed of a rubber material capable of holding cells, and a homogeneous subculture can be efficiently performed while maintaining the cells in an undifferentiated state and avoiding damages, from which cells can be selectively removed or recovered, and which has high processability and good visibility and thus enables the observation and examination of the cell state from the outside direction, and to provide a cell culture method using the same.

Means for Solving Problems

A cell-holding container of the present invention developed to achieve the objects described above comprises an elastic body for holding cells including at least any one of adherent cells at least one selected from the group consisting of stem cells, progenitor cells, somatic cells and germ cells, and suspended cells at least one selected from the group consisting of blood cells, T cells and B cells; and the elastic body is formed of a rubber material containing a rubber component including an additional crosslinking silicone rubber and is able to hold the cells.

In the cell-container, the stem cells are preferably induced pluripotent stem cells or embryonic stem cells.

In the cell-container, the cell-holding container may be used for cell culture.

In the cell-container, the additional crosslinking silicone rubber in the rubber material preferably includes filler having dry silica powder and/or wet silica powder.

In the cell-container, the additional crosslinking silicone rubber in the rubber material includes 5 to 40 parts by mass of filler having dry silica powder and/or wet silica powder relative to 100 parts by mass of the entire rubber component.

In the cell-container, the elastic body is preferably transparent.

In the cell-container, the elastic body preferably has up to 0.1 mm thickness, up to A40/S hardness according to Shore A hardness and up to 3.5 MPa tensile strength.

In the cell-container, a part of the elastic body may be sandwiched between a supporting member and a side wall member, and fixed by fitting up the supporting member and the side wall member.

In the cell-container, the elastic body may be reversibly deformable from a plain shape to a concave-convex shape having a dented concave part and/or a raised convex part by receiving external force.

In the cell-container, the elastic body may have a soft portion which is deformable and a hard portion which has undeformable properties.

In the cell-container, the soft portion preferably has up to 0.1 mm thickness.

In the cell-container, the elastic body is preferably opened at a cell contacting face side.

In the cell-container, the rubber component may be selected from the group consisting of an ethylene-propylene-diene rubber, a fluorocarbon rubber, a crosslinked silicone rubber and a fluorocarbon elastomer.

A cell culture method using the cell-holding container developed to achieve the objects described above comprises a step for deforming an elastic body of the cell-holding container from a plain shape to a concave-convex shape having a dented concave part after introducing a cell suspension, in which cells including at least any one of adherent cells at least one selected from the group consisting of stem cells, progenitor cells, somatic cells and germ cells, and suspended cells at least one selected from the group consisting of blood cells, T cells and B cells are dispersed into the cell-holding container; and a step for deforming the elastic body from the concave-convex shape to the plain shape after seeding the cells into the dented concave part and forming cell clusters.

Effects of the Invention

The cell-holding container of the present invention holds the cells such as the induced pluripotent stem cells or the embryonic stem cells on the elastic body formed of the rubber material containing at least the additional crosslinking silicone rubber as the rubber component, can form and culture the cell clusters through aggregating seeded cells, and can observe and examine these. Whether the elastic body of the cell-holding container has the plain-shaped state or the concave-convex-shaped state, visibility of the cell-holding container is not decreased. Therefore whether the cell-holding container is an opened-system container or a closed-system container, the cells held on the elastic body can be observed by using a microscope. Further according to the cell-holding container, the cell clusters having a homogeneous size can be formed on the elastic body which is deformed or formed into the concave-convex shape, and the subculture can be performed in the good efficiency without damaging the cells.

In the cell-holding container, the elastic body may have 0.1 mm thickness or less which is capable of reversibly deforming into a predetermined shape and it can exhibit excellent processability with such thinness. Thereby the elastic body shows excellent stretch, is capable of reversibly deforming into the predetermined shape, and returning to the original shape without strain. In addition, since the elastic body can be reversibly deformed at any timing, the visibility may be improved as needed and the cells may be held or cultured without mixing the air bubble into the cell-holding container.

According to the cell culture method of the present invention, the subculture may be homogeneously performed with the good efficiency while maintaining the undifferentiated state of the cells without damaging to the cells. Further according to the cell culture method, no air bubble is mixed into the wells of the cell-holding container, and the cells can be cultured through stabilizing an establishing position thereof. Furthermore since the elastic body of the cell-holding container can be selectively deformed, the visibility is excellent, and observation and examination of a cell state before and after culturing it or while culturing it can be conducted from the outside direction.

MODE FOR CARRYING OUT THE INVENTION

Hereunder, embodiments to practice the present invention in detail will be explained, but the scope of the present invention is not restricted by these embodiments.

According to an embodiment of a cell-holding container of the present invention, the opened-system cell-holding container comprises an elastic body formed of a rubber material. The opened-system cell-holding container is used in holding a master cell such as induced pluripotent stem cells (iPS cells) and embryonic stem cells (ES cells) on the elastic body and then, forming, culturing and observing cell clusters.

Figure 1:
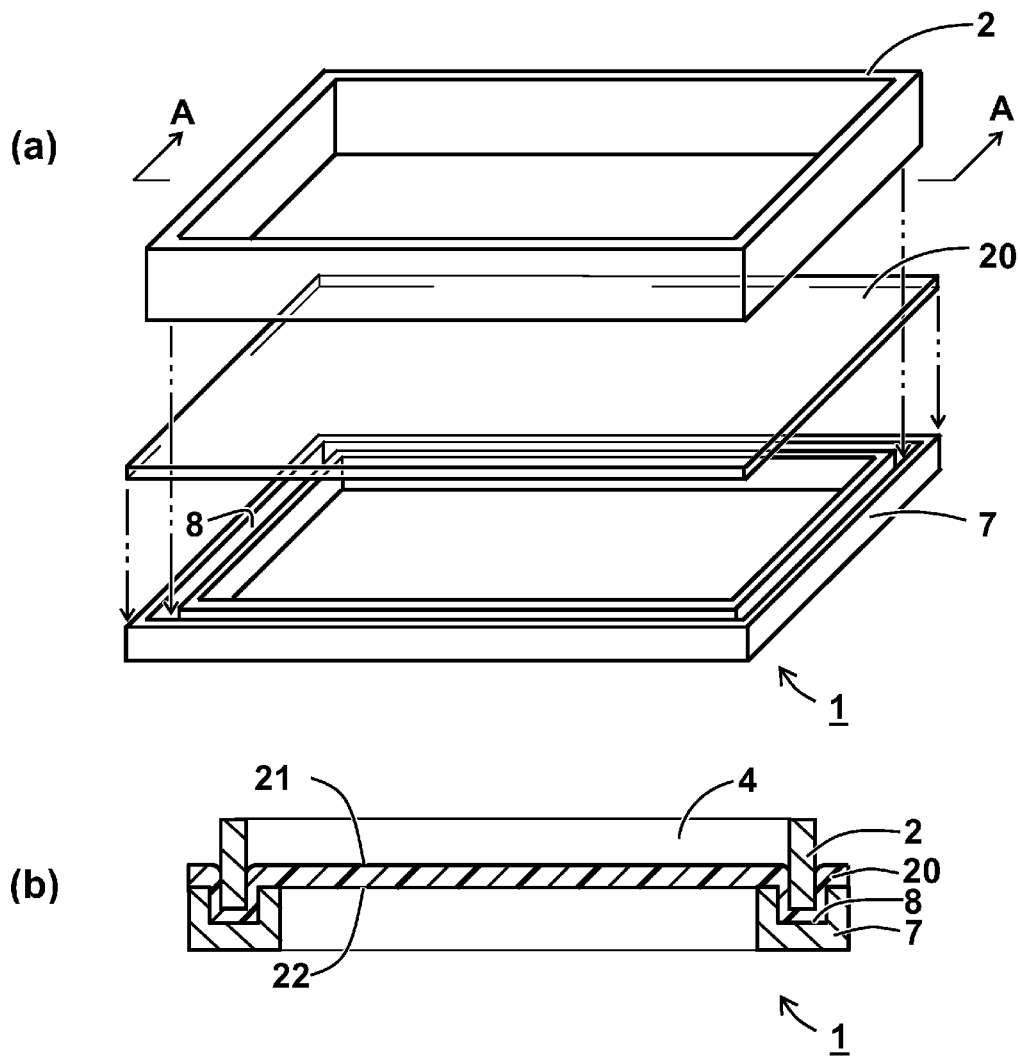
FIG. 1 is a schematic perspective view showing the cell-holding container of the present invention and a schematic cross-sectional view thereof taken along the line A-A.

The opened-system cell-holding container is explained while referring FIG. 1 showing an embodiment thereof.

The cell-holding container 1 of the present invention comprises the elastic body 20 formed of the rubber material, a side wall member 2 which surrounds a circumference thereof and a supporting member 7 fixing the electing body 20. As shown in FIGS. 1(a) and (b), since a part of the elastic member 20 is sandwiched between the supporting member 7 and the side wall member 2, and the side wall member 2 is fitted up a groove 8 of the supporting member 7, the elastic member 20 of the cell-holding container 1 is physically fixed.

In the cell-holding container 1, the sheet-shaped elastic body 20 is positioned on the frame-shaped supporting member 7 having the groove 8, and a part of the side wall member 2 is fitted in the groove 8 of the supporting member 7 from the above. Thereby the elastic member 20 may be fixed. The elastic body 20 is suitably tightened by having elasticity and stretch without straining and flexing. In the elastic body 20, a cell contacting face 21 holding the cells and a cell non-contacting face 22 which is an outer side and the counter side thereof are flat shapes. The cell-holding container 1 holds the cells by adhering it on the elastic body 20 and thus, the cells may be cultured, observed and examined. When the elastic body 20 is a bottom of the cell-holding container 1, the cells may be held in a part of the cell contacting face 21 encircled by the side wall member 2 as homogeneous or unhomogeneous dots, or the cells may be held in the cell contacting face 21 by immersing the entire cell contacting face 21 which is encircled by the side wall member 2. When the held cells are cultured, an inner side encircled by the side wall member 2 is used as a culturing chamber 4. In this cell-holding container 1, since the cell contacting face 21, i.e. the culturing chamber 4 is at an opened state, removing and recovering the cells are easy without a complex process and workability is high. Furthermore according to the cell-holding container 1, work may be effectively carried out while maintaining a cell state without damaging the cells.

The elastic body 20 forming the cell-holding container 1, is formed of the rubber material including at least additional crosslinking silicone rubber as a rubber component. The rubber component may be the additional crosslinking silicone rubber, may be a condensation silicone rubber or may include any of these silicone rubbers and a rubber at least one selected from the group consisting of an ethylene-propylene-diene rubber (EPDM), a fluorocarbon rubber and a fluorocarbon elastomer. The fluorocarbon rubber and the fluorocarbon elastomer may be kneaded in the rubber material without being melted. The elastic body 20 preferably consists of the additional crosslinking silicone rubber as the rubber component on the point of the view of the processability.

As the additional crosslinking silicone rubber, specifically, LSR7005, LSR7030, LSR7060, LSR7070 and LSR7080 (available from Momentive Performance Materials Inc.) are exemplified.

Filler may be included in the rubber material. The filler is preferably included in the additional crosslinking silicone rubber. When the ethylene-propylene-diene rubber (EPDM), a fluorocarbon rubber or a fluorocarbon elastomer except the additional crosslinking silicone rubber is included as the rubber component, the filler is preferably included in the rubber component except the fluorocarbon rubber and the fluorocarbon elastomer. For example, when the fluorocarbon rubber and the fluorocarbon elastomer are kneaded in the rubber material without melting, the filler may be included in the rubber component other than these.

As the filler, for example, dry silica powder, wet silica powder and mixture thereof are included. When the additional crosslinking silicone rubber as the rubber component is only employed, the dry silica powder is preferably included therein. The cells may be stably cultured on the elastic rubber 20 by including the filler. When the filler is included in the rubber material, adherability with respect to another member such as the side wall member described follows may be improved. The cell-holding container employing no filler, employing 20 phr the dry silica at a maximum or employing 5 phr the wet silica at a maximum exhibits extremely excellent culturability and visibility. The visibility of the cell-holding container employing 20 phr or more of the wet silica is somewhat decreased.

Though content of the filler depends to type of the filler and type of the rubber component, it is 40 parts by mass at a maximum, and is preferably 5 to 40 parts by mass relative to 100 parts by mass of the entire rubber component. When the content of the filler is higher than 40 parts by mass, the culturability is easily decreased. When the silica dry powder is employed, 0 to 20 parts by mass is preferred on the point of the view of the culturability. When the wet silica powder is employed, 0 to 20 parts by mass is preferred on the point of the view of the culturability, 0 to 5 parts by mass is preferred on the point of the view of the visibility. In the case of the embodiment including EPDM in the rubber component, when the dry silica powder is employed, 0 to 30 parts by mass is preferred on the point of view of the culturability.

When the wet silica powder is employed, 0 to 20 parts by mass is preferred on the point of the view of the culturability, 0 to 5 parts by mass is preferred on the point of the view of the visibility.

The elastic body 20 formed of the above rubber material preferably has the excellent visibility and transparency, and more preferably has colorless and transparency on the point of the view of facilitating a microscopy by using a phase contrast microscope etc. The filler added into the rubber material is preferably a little content as much as possible on the point of the view of transparency.

The elastic body 20 has the stretch, can be deformed as needed from a flat shape to a concave-convex shape when forming, culturing, observing and examining the cell clusters by holding the cells, is capable of returning to the original shape by eliminating these deformations, and may be reversibly deformed. The convex-concave shape refers to a shape having a plural or single dented part and raised part on a part of the elastic body 20. For example, when the external force is applied from the cell contacting face 21 toward the cell non-contacting face 22 relative to the elastic body 20, it is deformed to the convex-concave shape having the dented concave part. Crossly, when the external force is applied from the cell non-contacting face 22 toward the cell contacting face 21, it is deformed to the convex-concave shape having the raised convex part. The elastic body 20 can be deformed to a predetermined shape as needed, easily eliminates the deformation and returned to the original shape without strain. Thereby, corresponding to a situation, the elastic body 20 may be deformed to the convex-concave shape in order to form the cell clusters of the seeded cells, and can eliminate the convex-concave shape in order to improve the visibility when conducting observation and examination of the cultured cells.

Figure 2:
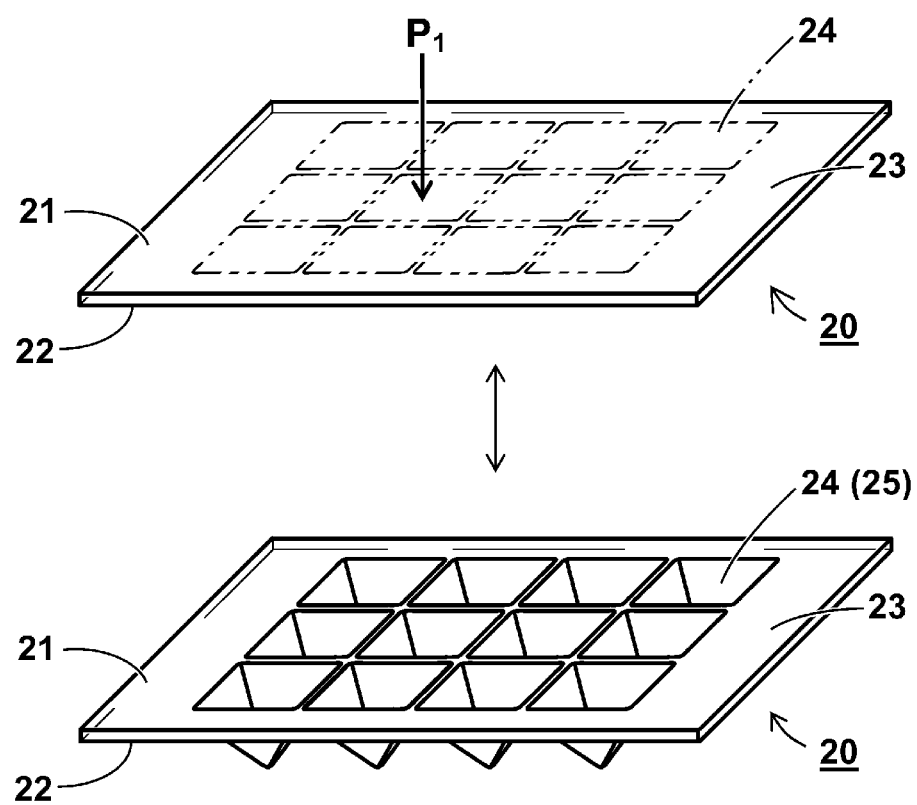
FIG. 2 is a schematic perspective view showing before and after deformation in the deformable elastic body of the cell-holding container of the present invention.

As one embodiment of the deformation, the elastic body 20 consisting of plural soft portions 24 and hard portion 23 is exemplified. For instance, as shown in FIG. 2, both of the cell contacting face 21 and the cell non-contacting face 22 of the elastic body 20 show flat shapes in a normal state. When an external force $P_1$ is applied to the cell contacting face 21, the hard portions 23 are not deformed. The plural soft portions 24 are stretched toward the outside direction and are deformed so as to form the dented parts 25 having an opened-four-sided pyramid. Further, when the external force $P_1$ is removed, the deformation is eliminated, and then it is returned to the original shape without strain. The dented parts 25 which are formed as mentioned above can hold the cells and thus, the cell clusters can be formed, cultured and observed.

The dented parts 25 may be used as the wells to form the cell clusters. The wells may be termed to "micro wells" in order to distinguish from wells which lay out a culturing hole of a multi plate used in a general cell culture, it is not a term which intends to except wells having an opening part including a diameter or a side of 1mm or more. The wells having the opening part including the diameter of the side of 1 mm or more are included therein. In addition, the micro wells may be also referred to "dented part" hereinafter.

According to the micro wells, the cells of the cell suspension injected into the cell-holding container 1 are deposited by the force of gravity etc., and then the deposited cells aggregate on a bottom face of the wells. Thereby the cell clusters may be formed. The micro wells have a shape for aggregating the deposited cells. A shape of an inner circumference thereof is preferably tapered off as approaching a bottom thereof. For example, a cone bottom, a round bottom, a V-shaped bottom and a U-shaped bottom are preferred, a four-sided pyramid bottom is more preferred. In addition, a shape of the micro wells which is molded on a plate bottom of Aggrewell (trademark) (available from STEMCELL Technologies Inc.) is preferred.

The micro wells preferably have a slope face which is polished to a mirrored surface. A tip part which is an apex of the dented part preferably has the round shape. A size of the micro wells may be appropriately selected corresponding to the intended cell clusters. This size larger than the intended cell clusters may be selected.

Though a shape of the opening part of the micro wells is appropriately selected through considering processability and a shape which can arrange the wells in large numbers, it may have a circular shape or a polygonal shape such as a triangular shape, a square shape or a hexagonal shape etc.

A size of the opening part of the micro wells can be selected depending on the size of the cell clusters which should be formed. For instance, the opening part may have an area which is equivalent to a circle area having a diameter from 100 μm to 3 mm, from 200 μm to 800 μm or 400 μm to from 600 μm.

The preferred size of the cell clusters, which are formed, is mutually equivalent. In the plural micro wells which are formed on the elastic body 20, the preferred shape and size are mutually same in order to equalize the size of the cell clusters which are formed. Comparably homogeneous dispersion of the cells is easily achieved in the micro wells and thus, the cell clusters having the homogeneous size can be formed.

In order to obtain huge amount of the cell clusters, the micro wells are preferably formed at the elastic body 20 so as to be arranged in large numbers. The preferred micro wells are closely and regularly paralleled and arranged without an interspace so as to form no flat space between the adjacent wells or with a minimum distance therebetween. In order to uniformly seed the cell clusters, which are formed through a cell culture method, to a culture face, the micro wells are preferably aligned with equally spaced intervals on a plain face.

Figure 3:
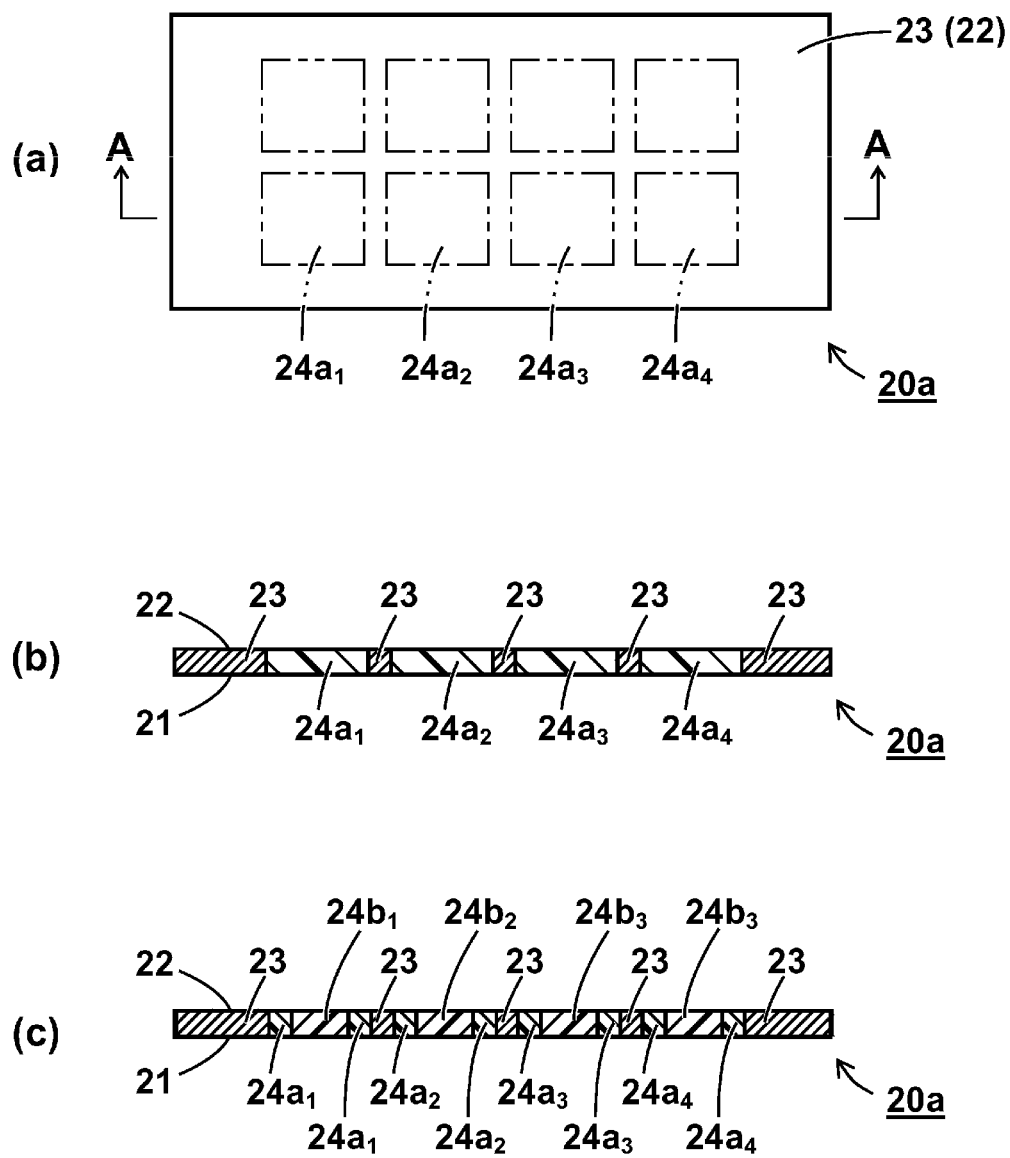
FIG. 3 is a schematic plain view showing another deformable elastic body of the cell-holding container of the present invention and a schematic cross-sectional view thereof taken along the line A-A.
Figure 4:
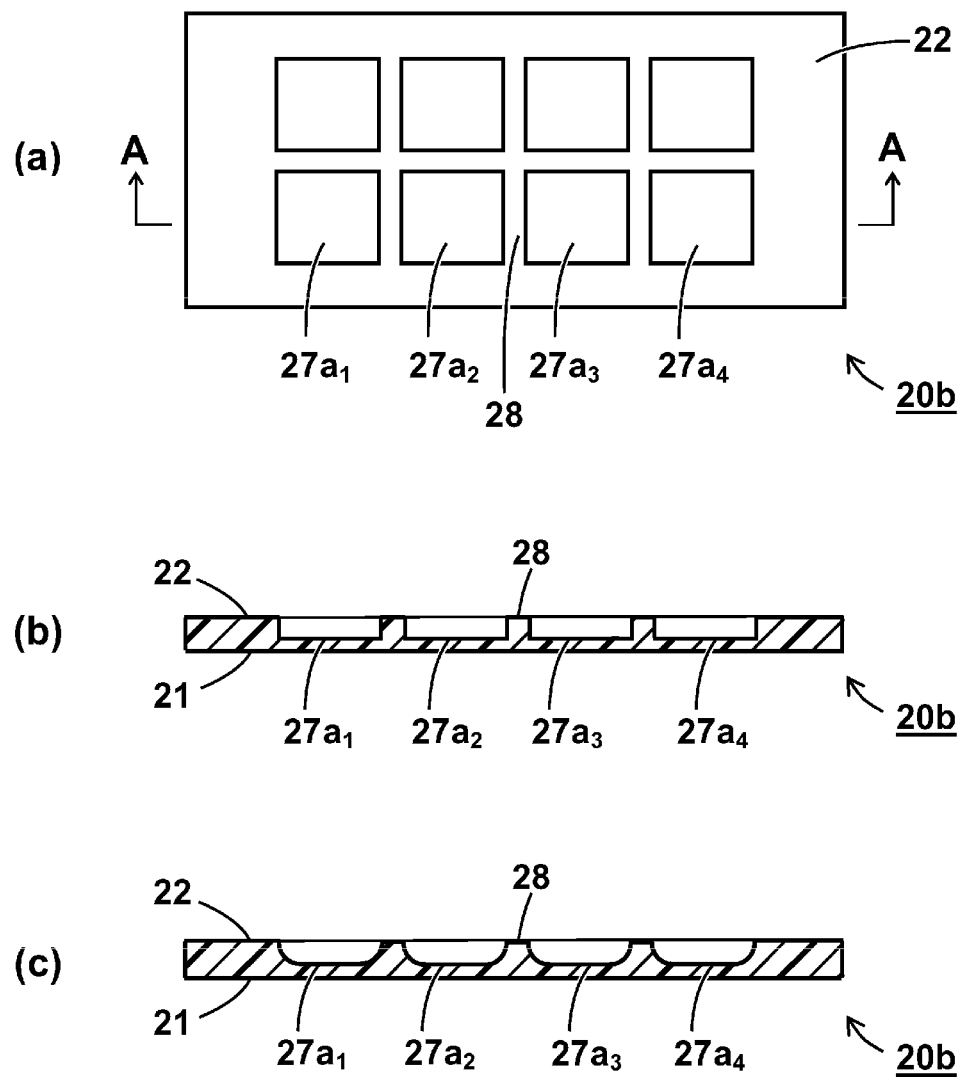
FIG. 4 is a schematic plain view showing another deformable elastic body of the cell-holding container of the present invention and a schematic cross-sectional view thereof taken along the line A-A.
Figure 5:
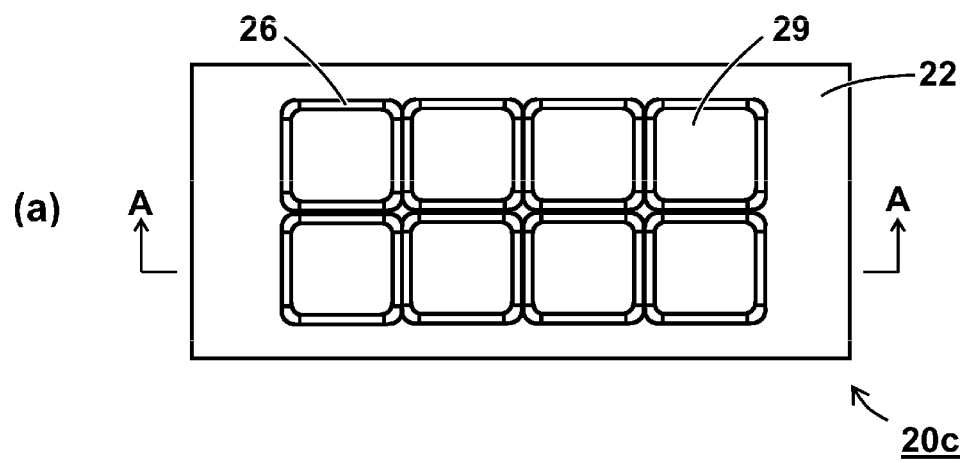
FIG. 5 is a schematic plain view showing another deformable elastic body of the cell-holding container of the present invention and a schematic cross-sectional view thereof taken along the line A-A.

The deformable elastic body 20 can be deformed to a predetermined shape. As shown in FIG. 3, the elastic body 20 may be an elastic body 20a consisting of the plural soft portions 24 and the hard portion 23. As shown in FIG. 4, the elastic body 20 may be an elastic body 20b having partially different thicknesses. As shown in FIG. 5, the elastic body 20 may be an elastic body 20c provided with a hard frame 26 forming plural opening parts 29.

FIG. 3(a) is a schematic plain view showing the cell non-contacting face 22 of the elastic body 20a having the soft portions 24 which are deformable zones and the hard portion 23 which is undeformable zone. FIG. 3(b) is a schematic cross cross-sectional view thereof taken along the line A-A therein. For example, when external force aspirating the cell non-contacting face 22 is applied, the hard portion 23 is not deformed as shown in FIG. 2 and, for instance, the plural soft portions $24a_1$, $24a_2$, $24a_3$, $24a_4$ existed within respective squares or grids thereof are attracted, and stretched toward the outside direction while forming the dented concave parts and deformed. Reversely, when external force pressurizing the cell non-contacting face 22 is applied, the hard portion 23 is not deformed in the same as above, and the soft portions $24a_1$, $24a_2$, $24a_3$, $24a_4$ are compressed, and stretched toward an inside direction while forming the raised convex parts and deformed.

As shown in a schematic cross-sectional view of FIG. 3(c), in order to sharpen the tip part (a bottom end) formed by deforming which is the apex of the dented part of the micro wells, the elastic body 20a has the hard portion 23 being the undeformable zone and the soft portions 24 being the deformable zones, and these hardness may be gradually varied. A membrane of the elastic body 20a may be processed so that the hardness of the membrane is gradually decreased from the soft portion $24a_1$ to the soft portion $24b_1$, provides with a minimum hardness at the soft portion $24b_1$ forming the bottom end of the micro wells, is gradually increased therefrom to the soft portion $24a_1$, and provides with a maximum hardness at the hard portion 23 being the undeformable zone. When the elastic body 20a receives external force, for example, the soft portions $24a_1$, $24a_2$, $24a_3$, $24a_4$ and $24b_1$, $24b_2$, $24b_3$, $24b_4$ are deformed, e.g. in the shape of a four-sided pyramid shape having the soft portions $24b_1$, $24b_2$, $24b_3$, $24b_4$ as an apex of the dented part, without deformation of the hard portion 23 which is plural squares or grids like shape and has square shaped pockets. The hard portion 23 may have circle shaped pockets arranged in a matrix, and the pockets may be the soft portions.

In the elastic body 20 having the hard portion 23 and soft portions 24, the hardness of the elastic portion 20 is optimized. As long as no shape variation by external force occurs in the hard portion 23, the hard portion 23 may be formed of the same rubber material as the soft portions 24, and may be formed of different member therefrom. The elastic body 20 may be formed by using known methods such as an insert molding method.

FIG. 4(a) is a schematic plain view showing the cell non-contacting face 22 of the elastic body 20b forming high and low thicknesses so as to become the deformable zones which are thinner than the undeformable zone having e.g. a plural squares or grids like shape. FIG. 4(b) is a schematic cross cross-sectional view thereof taken along the line A-A therein. The elastic body 20b is processed so that the cell contacting face 21 is flat, and thin portions 27 are formed into the deformable zones so as to be a different thickness between the deformable zones and the undeformable zone in the cell non-contacting face 22. For example, when external force which aspirates the cell non-contacting face 22 is applied, thick portion 28 as undeformable zones is not deformed, and the plural thin portions $27a_1$, $27a_2$, $27a_3$, $27a_4$ are attracted, stretched toward the outside direction while forming the dented concave parts and deformed. Reversely, when external force pressurizing the cell non-contacting face 22 is applied, the thick portion 28 as the undeformable zone is not deformed in the same as above, and the thin portions $27a_1$, $27a_2$, $27a_3$, $27a_4$ are compressed, stretched toward an inside direction while forming the raised convex parts and deformed.

As shown in a schematic cross-sectional view of FIG. 4(c), in order to steeple the bottom end of the micro wells which are formed by deforming, the deformable zones and the undeformable zone mutually have the respectively different thickness, and the thickness from the deformable zones to the undeformable zone in the elastic body 20b may be gradually varied. The elastic body 20b may be processed so that the thickness is gradually decreased from the thick portion 28 as the undeformable zone to the apex of the dented part, becomes a minimum at a part which forms the bottom end of the micro wells, and is gradually increased therefrom to the thick portion 28.

FIG. 5(a) is a schematic plain view showing the cell non-contacting face 22 of the elastic body 20c which is provided with e.g. the approximately square-shaped hard frame 26 forming the plural opening parts 29. FIG. 5(b) is a schematic cross cross-sectional view thereof taken along the line A-A therein. The hard frame 26 corresponds to the undeformable zone, and zones with respect to the opening parts 29 of the hard frame 26 correspond to the deformable zones. For example, when external force aspirating the cell non-contacting face 22 is applied, the zones with respect to the opening parts 29 can be deformed, stretched toward an outside direction while forming the dented concave parts in the cell-contacting face 21 and deformed.

As shown in FIGS. 3 to 5, although a deformable elastic body which is formed so as to reversibly deform by receiving external force is exemplified, the elastic body 20 may be an undeformable elastic body which is molded or formed so as to have a predetermined shape such as a concave-convex shape or a flat shape through a preliminarily forming process by using a mold.

The preferred hardness of the deformable or undeformable elastic body 20 is A5/S to A90/S conforming to Shore A hardness. Especially, the hardness of the deformable elastic body 20 preferably has A40/S or less. In the case of higher than A40/S, adhesiveness is easily decreased. When the hardness of the elastic body 20 is partially optimized as shown in FIGS. 3(b) and (c), the hardness of the deformable zone is preferably A5/S to A30/S, the hardness of the undeformable zone is preferably A50/S to A90/S.

The thickness of the deformable or undeformable elastic body 20, is not especially restricted, is preferably 0.05 mm to 2.00 mm. Especially the thickness of the deformable elastic body 20 is preferably 0.1 mm or less. In the case of higher than 0.1 mm, the deformation is difficult. When the thickness of the elastic body 20 is partially optimized as shown in FIGS. 4(b) and (c), the thickness of the deformable zone is preferably 0.05 mm to 0.30 mm, the thickness of the undeformable zone is preferably 0.50 mm to 2.00 mm.

Preferred tensile strength of deformable the elastic body 20 is 3.5 MPa or less. In the case of higher than 3.5 MPa, when the external force as mentioned above is applied, aspiration is difficult.

In the cell-holding container 1, as long as the cell contacting face 21 of the bottom is the elastic body 20 formed of the rubber material, the bottom, the side wall member 2 and the supporting member 7 may be formed of a same or different material respectively, may be rubber products formed of the similar rubber material, or may be plastic products made of a plastic material such as polystyrene, polypropylene, polycarbonate and an acryl resin.

In the cell-holding container 1, when the supporting member having the groove and plural grids like shape, and the side wall member having grids like shape which is capable of fitting up the groove are used, the cell contacting face 21 may be plurally partitioned. The cell-holding container 1 may be a flat dish such as a Petri dish having the elastic body 20 which is formed of the rubber material and is the bottom, and the side wall member 2 which surrounds the circumference thereof. In this cell-holding container 1, the plain-shaped elastic body 20 and the side wall member 2 may be chemically adhered and fixed through an adhesive such as an acryl-modified silicone resin. In the elastic body 20 of the cell-holding container 1, both of the cell contacting face 21 and the cell non-contacting face 22 have the flat shape as mentioned above. The shape of the cell-holding container 1 is not restricted, various shapes such as a circular shape, an oval shape and a polygonal shape are included.

The elastic body 20 is an elastomer for an adherent culture of iPS cells and ES cells. The cell-holding container 1 is suitably used in forming, culturing, observing and examining the cell clusters through aggregating at least any theses cells. The cell-holding container 1 can be also used in aggregating, forming the cell clusters, culturing, observing and examining adherent cells, suspended cells and the like. As the adherent cells, pluripotent stem cells, stem cells, progenitor cells, somatic cells and germ cells are included. As the suspended cells, blood cells, T cells and B cells are included. The preferred suspended cells are T cells and B cells.

Figure 6:
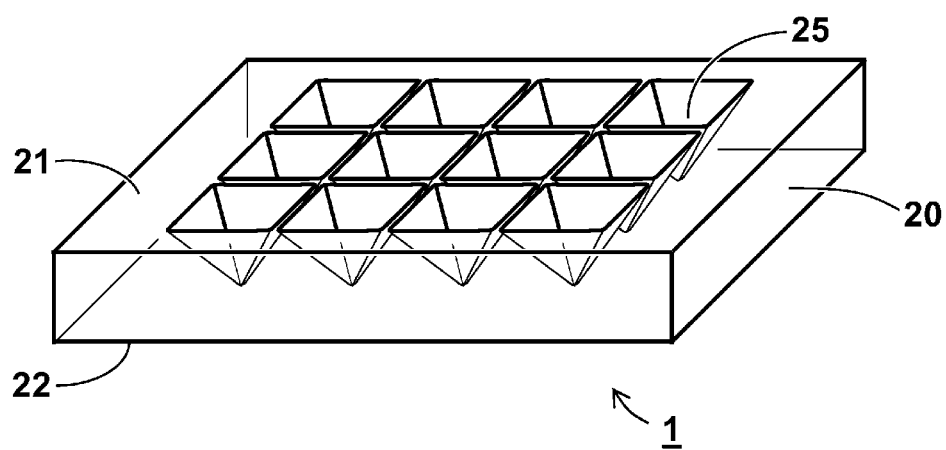
FIG. 6 is a schematic perspective view showing another cell-holding container of the present invention.

As shown in FIG. 6, the cell-holding container 1 of the present invention may be a plate consisting of the elastic body 20 formed of the rubber material. The cell contacting face 21 being an upper side of the plate may have the concave-convex shape including the plural dented parts 25 with the four-sided pyramid shape, and the cell non-contacting face 22 being a lower side thereof may have the flat shape. The cell contacting face side is opened. The cell-holding container 1 holds the cells in the dented parts 25 of the elastic body 20. The seeded cells are aggregated by depositing in the dented parts 25. Thus the cell clusters may be formed, cultured, observed and examined.

The cell non-contacting face 22 of the elastic body 20 is not restricted in the flat shape, and may have the concave-convex shape corresponding to the cell contacting face 21. The cell non-contacting face 22 is preferably polished through a mirror finishing. The elastic body 20 may be the deformable elastic body or the undeformable elastic body.

Figure 7:
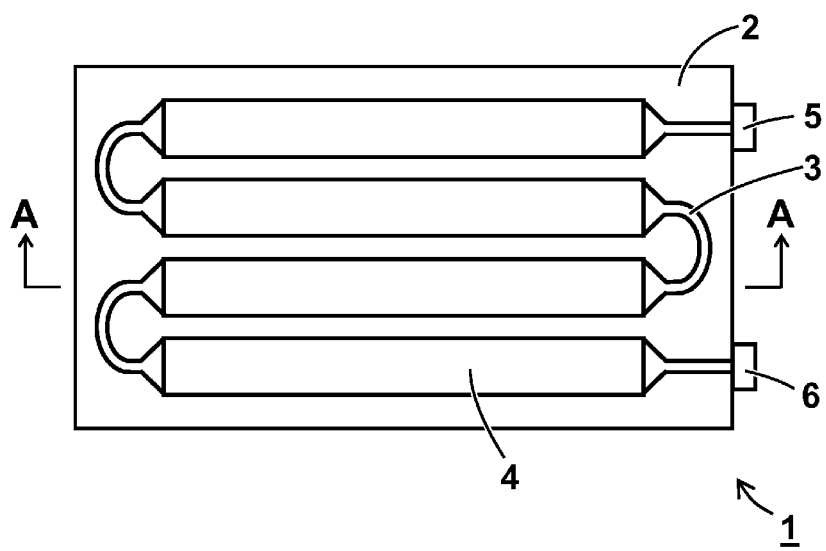
FIG. 7 is a schematic plain view showing another cell-holding container of the present invention.
Figure 8:
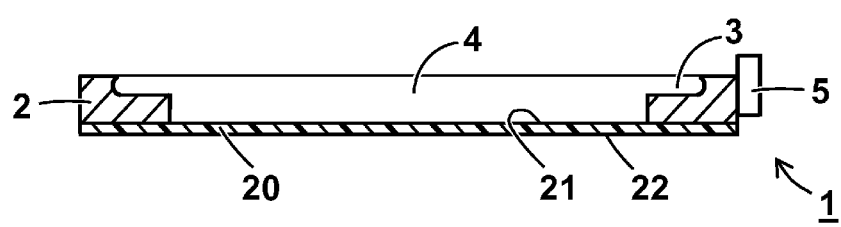
FIG. 8 is a schematic cross-sectional view in FIG. 7 taken along the line A-A.

Furthermore another cell-holding container is explained referring to FIGS. 7 and 8 showing the embodiment thereof. FIG. 7 is a schematic plain view showing an upper side of the cell-holding container. FIG. 8 shows a schematic cross-sectional view of FIG. 7 taken along the line A-A.

The cell-holding container 1 has an injection hole 5 and a drain hole 6. The culturing chambers 4 and flow paths 3 are formed by the elastic body 20 and the side wall member 2. The cell-holding container 1 may be produced as follows. The side wall member 2 which forms the culturing chambers 4 and the flow paths 3 is adhered onto the elastic body 20 having the plain shape through an adhesive such as an acryl-modified silicone resin. In the culturing chambers 4 of the cell-holding container 1, a whole or partial surface of the cell contacting face 21 being an inner face of the elastic body 20 preferably has cell adherability.

A cell-containing solution such as the cell suspension and cell-culturing solution for a culture medium are sent and filled in the culturing chambers 4. A cell-releasing solution, a cell-recovering solution and the like are sent therein as needed.

In the cell-holding container 1, the plural culturing chambers 4 is connected through the flow paths 3, and the injection hole 5 and the drain hole 6 of the solution which is sent are formed. The injection hole 5 is an inlet of the solution which is sent, and the drain hole 6 is an outlet thereof. The solution sent from the injection hole 5 is flowed into the culturing chamber 4 from one of the flow path 3 which is formed into both ends of the culturing chamber 4, and then is flowed out through the other flow path 3. The solution is continuously flowed into the next culturing chamber 4, is flowed out through the flow path 3 connected thereto, and is finally drained by irreversible flow through the drain hole 6. According to the stably irreversible flow, the cells can be homogeneously seeded into the culturing chambers 4 by injecting the cell suspension into the cell-holding container 1. In addition according to the stably irreversible flow, the cell-culturing solution, which is sent to culture the seeded cells, is homogeneously perfused by the stably irreversible flow.

A constituent of the cell-holding container 1 is not restricted to the constituent in which the plural culturing chambers 4 are connected via the flow paths 3. The respective culturing chambers 4 are provided with the injection hole 5 and the drain hole 6 through the flow path 3 and may be independently formed. The culturing chamber 4 is not restricted to a plurality, and may be a single. The injection hole 5 and the drain hole 6 are not to need independently, may be integrated.

In the elastic body 20 for the cell-holding container 1, both of the cell contacting face 21 and the cell non-contacting face 22 may be the deformable elastic body which is formed to the plain shape having the flat shape, or may be the undeformable elastic body which is preliminarily processed by using a mold.

According to the deformable elastic body 20, at least a region to form the culturing chamber 4 is deformable. As the elastic body 20, the deformable elastic bodies 20a, 20b, 20c as shown in FIGS. 3 to 5 may be employed in the same as above. When the cell clusters are formed by seeding the cells, cultured, observed and examined, the region which forms the culturing chamber 4 can be deformed from the flat shape to the concave-convex shape as needed, can be reversed to the original shape by eliminating these deformations and can be reversibly deformed. For example, when external force directing the culturing chamber 4 from the cell non-contacting face 22 of the elastic body 20 is applied thereto, the whole or partial region forming the culturing chamber 4 in the elastic body 20 is deformed to the concave-convex shape having the raised convex parts toward the culturing chamber 4. Reversely, when external force directing an outer direction of the elastic body 20 from the cell contacting face 21 of the elastic body 20 is applied thereto, the whole or partial region forming the culturing chamber 4 in the elastic body 20 is deformed to the concave-convex shape having the dented concave parts toward the culturing chamber 4. Because predetermined shape variation is capable as needed, and the shape can be returned without strain by easily eliminating the shape variation, the visibility can be improved by eliminating the concave-convex shape when conducting observation and examination of the cultured cells, and the culture medium, a reagent and a specimen can be economized by eliminating the concave-convex shape while corresponding to a situation.

In the undeformable elastic body 20, the cell contacting face 21 is preliminarily molded to the concave-convex shape. The cell non-contacting face 22 may have the flat shape and may have the concave-convex shape corresponding to the cell contacting face 21. In the concave-convex shape of the cell contacting face 21, the dented parts 25 having the opened-four-sided pyramid are plurally formed into the region forming the culturing chamber 4 of the cell contacting face 21. The slope face of the dented parts 25 and the cell non-contacting face 22 are preferably polished to the mirror surface, respectively.

The dented parts 25 of the deformable or undeformable elastic body 20 in the cell-holding container is similar to the micro wells of the cell-holding container which is exemplified above, can hold the cells, and can be used in the formation, culture and examination of the cell clusters.

The side wall member 2 may be formed of the same or similar rubber material as the elastic body 20, or may be formed of a different material therefrom. Further, the preferred side wall member 2 is transparent having the excellent visibility on the point of the view of a microscopy.

When the elastic body 20 and the side wall 2 are mutually formed of the similar rubber material, the visibility is improved due to a relationship between a reflective index of the rubber material and a reflective index of the cell-culturing solution (a culture medium) filling the culturing chamber 4 and thus, the microscopy can be easily carried out. Since the cell-culturing solution (the culture medium) filling the culturing chamber 4 mostly includes water, the reflective index thereof is 1.33. The reflective index of the additional crosslinking silicone rubber is 1.40 to 1.43. Thus an appearance of the culture of the cells can be directly observed from the outside direction of the cell-holding container 1, and the observation using a microscope can be easily conducted.

The side wall member 2 is not restricted to the rubber products formed of the rubber material, and may be the plastic products formed of polystyrene, polypropylene, polycarbonate, an acryl resin and the like.

The culturing chamber 4 of the cell-holding container 1 preferably has the cell adherability at a face for an adhesion of the cells, and preferably has cell non-adherability except that face. In the culturing chamber 4, the whole or partial dented parts 25 which is formed or molded so as to become the wells may have the cell adherability. The cell adherability may be selectively imparted to necessary parts thereof. In the culturing chamber 4, when the slope face of the dented parts 25 has the cell adherability, the cell can be established on the slope face. When the slope face of the dented parts 25 does not have the cell adherability, the cells can be aggregated in the apex of the dented parts 25 without establishing the cells on the slope face. The cell non-adherability may be selectively imparted to other face except the face for an adhesion of the cells. In the face except the other face for an adhesion of the cells, the adhesion thereof is prevented and thus, the cell clusters can be effectively released after forming it.

The cell adherability can be imparted to a cell adhesive face by a cell adherability coating. As the cell adherability coating, for example, a basement membrane matrix having the cell adherability such as Matrigel (trademark) (available from Nippon Becton, Dickinson Co., Ltd.) may be used. Thereby the cell adherability coating can be applied to an adhesive face. As a coating method using a coating agent available in the market, a known method may be employed. The cell adherability may be imparted by irradiating ultraviolet (UV) and/or plasma.

The cell non-adherability can be imparted to a cell non-adhesive face by a cell non-adhesive coating. The cell non-adherability coating is not restricted as long as a coating having the cell non-adherability. For example, celluloses such as methyl cellulose, hydroxyethyl cellulose, hydroxypropyl cellulose, hydroxypropylmethyl cellulose and sodium carboxymethyl cellulose; polyethylene oxide; carboxyvinyl polymer; polyvinylpyrrolidone; polyethylene glycol; polylactic acid; polyamide such as polyacrylamide and polyN-isopropylacrylamide; polysaccharide such as chitin, chitosan, hyaluronic acid, alkyd acid, starch, pectin, carrageenan, guar gum, gum arabic and dextran; and cell non-adherability derivatives of them are exemplified. Polyethylene glycol is preferred on the point of the view of the high transparent and the excellent visibility.

The cell-holding container 1 of the present invention may be provided with a covering member such as a cover, a film, a sheet, a plate and substrate which temporarily covers the cell contacting face 21, the culturing chamber 4 and the flow path 3 as needed, and is capable of attaching and removing. In the cell-holding container, the covering member such as the substrate having the plain shape, which seals and glues up the culturing chamber 4 and the flow path 3 opposite to the cell contacting face 21 of the elastic body 20, may be come into contact therewith and may be adhered so as to be closed and not attaching and removing. According to the cell-holding container 1, for example, the side wall member 2 forming the culturing chamber 4 and the flow path 3 is existed and adhered between the elastic body 20 having the plain shape and the substrate being the cover member having the plain shape which is arranged opposite thereto. The culturing chamber 4 is formed by the elastic body 20 and the substrate. When a surface of any of an inner face of the elastic body 20 and an inner face of the substrate has the cell adherability, the culturing chamber 4 having the cell adhesive face may be formed. Further, when the surface any one of the inner face of the elastic body 20 and the inner face of the substrate has the cell adherability and the other inner face has the cell non-adherability, the culturing chamber 4 in which the cell adhesive face and the cell non-adhesive face are faced and arranged may be formed. The cell adherability may be imparted to the whole or partial surface in any of the inner face of the elastic body 20 and the inner face of the substrate. In addition, the cell adherability may be imparted to the whole or partial region forming the culturing chamber 4.

The covering member may be the rubber products formed of the same or similar rubber material as the elastic body 20, and may be the plastic products formed of polystyrene, polypropylene, polycarbonate, an acryl resin and the like. The preferred covering member is a gas-transmissive membrane on the point of the view of maintaining concentration of oxygen and carbon dioxide in the culturing chamber 4. For example, the polystyrene made gas-transmissive membrane for cell culture available in the market may be used. The gas-transmissive membrane plays an important role to supply oxygen etc. to the culture medium in the culturing chamber 4. According to the cell-holding container 1 employing the gas-transmissive membrane as the covering member, the cells may be effectively released form a surface of the membrane by using ultrasonic vibration when the cultured cells by using the cell culture method are recovered. It is advantageous that more choices of a cell releasing method can be chosen.

In the case of using the cell-holding container 1, the culturing chamber 4 and the flow path 3 are filled with the cell suspension and the cell-culturing solution. Since a capacity of the culturing chamber 4 is varied by the deformation of the elastic body 20, adjusting it by draining from the drain hole 6 is needed. When the covering member is formed of the similar rubber material, the capacity variation by deforming the elastic body 20 to the concave-convex shape may be absorbed through extending and contracting of the cover member. Thereby even when the elastic body 20 is deformed to the concave-convex shape after sealing the injection hole 5 and the drain hole 6 by using a rubber plug, a solution leakage risk from the injection hole 5 and the drain hole 6 may be avoided.

The cell-holding container 1 of the present invention may be used as a cell-holding system for forming, culturing, observing and examining the cell clusters by aggregating the cells on the elastic body 20 made of the rubber material. The cell-holding system may be provided with the cell-holding container 1, a deforming means to deform the elastic body 20 thereof. According to the cell-holding system, the cells of the adherent cells and the suspended cells can be held on the elastic body 20, and a maintenance culture and a subculture can be homogenously and efficiently performed.

The cell culture method using the cell-holding container 1 is explained as follows.

The cell culture method of the present invention has steps in the order mentioned as follows: deforming the elastic body 20 of the cell-holding container 1 from the plain shape to the concave-convex shape having the dented parts 25 after introducing the cell suspension dispersing the cells into the cell-holding container 1; and deforming the elastic body 20 so as to return the concave-convex shape to the plain shape after forming the cell clusters by seeding the cells to the dented parts which are formed by deforming the elastic body 20.

Cells 90 which are dispersed in the subculture may include cell masses (hereinafter may be referred to as just "cells"). In the adherent culture, the pluripotent stem cell which is released form the cell adhesive face by using a physiological or physical method may be used.

As the physiological method to release the pluripotent stem cell from the cell adhesive face, known methods may be used. For example, a method using an enzyme and a method using chemical substances having a cell releasing effect are exemplified.

The enzyme which is used in conventional methods may be used. As the enzyme, trypsin, dispase, accutase and collagenase are included. As the chemical substance having the cell releasing effect, a chelate agent for a bivalence ion (especially $Mg^{2+}$) such as et hylenediaminetetraacetic acid (EDTA) is included. The enzyme and the chelate agent having the cell releasing effect may be used either alone or conjunction.

As the physical method to release the pluripotent stem cell from the cell adhesive face, known methods may be used. For example, a method applying vibrations such as high frequency vibration to the adherent face of the cells and a method using a cell scraper are included. The physiological method and the physical method is appropriately selected and may be used either alone or conjunction.

The cell masses may be dissociated into a single cell level. The dissociation of the cell masses may be simultaneously conducted with releasing the cells from the culture face, or may be conducted after releasing the cell masses.

In dispersing the cells 90, when the cells released from the adhesive face maintain a shape of the cell masses, the cell masses released therefrom may be dispersed after dissociating it into the single cell level by a water flow of the pipette. The wordings "dispersing to the single cell level" define dispersing the cell masses after being dissociated into 1 to 100, preferably 1 to 10 of an average number of the cells per the cell masses, and also include dispersing after completely dissociating into the single cell. The cell masses may be dispersed after being dissociated so as to completely become the single cell, and may be dispersed after being dissociated so as to mostly become the cell masses including a number of 1 to 100 preferably 1 to 10 cells. According to the large cell masses after being dispersed, when the cell masses are seeded into the micro wells, a number of the cells which are seeded into the micro wells is easily varied. The cell masses after being dispersed therefore preferably has small size.

In addition the cell masses which are released from the culture face may be dispersed to the single cell level through an additional treatment by using the enzyme. As the enzyme which can be employed to dissociate the cells to the single cell level, known enzymes are employed. For example, an enzyme which is capable of cleaving a bond between the cells and an enzyme which is capable of cleaving a bond between cells-extracellular matrixes (ECM) are included. The dissociation of the cells using the enzyme or the water flow can be automated.

After dissociating the cells to the single cell level and dispersing them, a compound inhibiting a negative effect by dispersing them relative to the cells such as cell death, e.g. a ROCK inhibitor such as Y-27632, may be added into a suspension of the dispersed cells 90.

Figure 9:
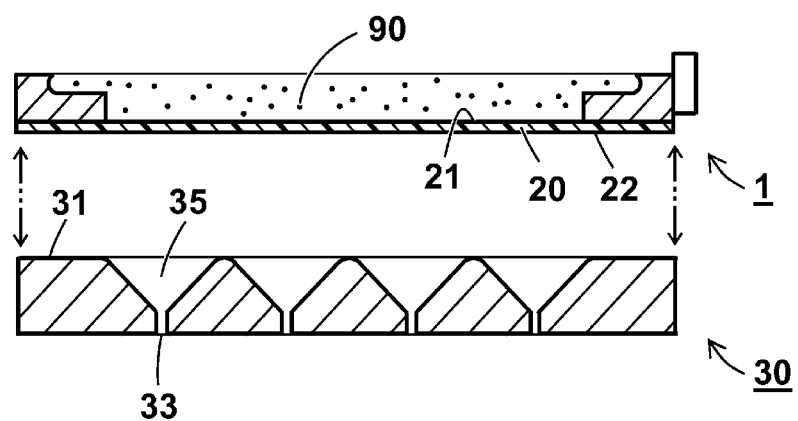
FIG. 9 is a schematic cross-sectional view showing a step of deforming the elastic body of the cell-holding container in the cell culture method of the present invention.

A deforming step of the elastic body 20 after introducing the suspension of the dispersed cells 90 into the cell-holding container 1 is show in FIG. 9. According to a cell-holding system in which a deforming means 30 to deform the elastic body 20 is arranged in an external side thereof, the elastic body 20 can be deformed by aspirating it under reduced pressure. Similarly, in a step of deforming step of the elastic body 20 to return the concave-convex shape to the plain shape after forming the cell clusters by seeding the cells into the formed dented parts, the deformation of the elastic body 20 can be released by eliminating a reduced state. The elastic body 20 going through the release of the deformation can be returned to the original plain shape while holding the cell clusters in the cell contacting face 21 without strain. Thereby because the deformation is released, the visibility in the observation can be greatly improved.

As shown in FIG. 9, the deforming means 30 has an aspiration-insufflation hole 33 aspirating or insufflating it by an aspiration-insufflation means which is connected to a concave-convex face 31 being a face opposite to the cell non-contacting face 22 of the elastic body 20 of the cell-holding container 1 and the single or plural dented part 35. The concave-convex face 31 being the face opposite to the cell non-contacting face 22 of the elastic body 20 of the cell-holding container 1 is opened opposite to the cell non-contacting face 22, and has the concave-convex shape in which the plural dented parts 35 are regularly formed so as to dent with a four-sided pyramid. An apex of the respective dented parts 35 (an apex of the four-sided pyramid) has the aspiration-insufflation hole 33. Since a part of the concave-convex face 31 is contacted with the cell non-contacting face 22 of the elastic body 20 of the cell-holding container 1, a vacuum chamber constituted by the respective dented parts 35 is formed between the elastic body 20 and it. According to the vacuum chamber, the shape of the elastic body 20 can be deformed through reducing or applying pressure using the aspiration-insufflation means. When the aspiration is carried out through the aspiration-insufflation hole 33, the vacuum chamber becomes a reduced pressure state. Further, when the insufflation is carried out therethrough, the vacuum chamber becomes a pressured state. The aspiration-insufflation means may aspirate the air from the vacuum chamber, and may insufflate the air to the vacuum chamber. A vacuum refers to a state where pressure is reduced from atmospheric pressure.

EMBODIMENTS

Embodiments of the present invention will be described in detail below, but the scope of the present invention is not restricted to these embodiments.

(Example 1)

A rubber plate having 0.05 mm thickness made of a rubber material of an additional crosslinking silicone rubber (available from Momentive Performance Materials Inc.) as an elastic body was adhered to a polyethylene made culturing container by using a silicone adhesive (available from CEMEDINE CO., LTD.; CEMEDINE SUPER X). Thereby a cell-holding container was obtained. Cells were seeded onto the rubber plate. As filler to add into the rubber material, wet silica powder (available from TOSOH SILICA CORPORATION; NIP SIL VN3) and dry silica powder (available from NIPPON AEROSIL CO., LTD.; AEROSIL 200) were used. GL15 sterilization lamp (available from TOSHIBA CORPORATION) was used for a UV sterilization treatment. In an irradiation conditions, a distance was 1 m, and an irradiation time was 24 hours. Results of the UV treatment about the respective rubber plates, visibility by using a microscope, processability in the rubber plate having thickness of 0.1 mm or less and results of observation using the microscope of a culture state are shown in Table 1 as below.

(Comparative Example 1)

A cell-holding container was produced through the method and the conditions in the same as Example 1 except that EPDM (available from JSR Corporation) and a fluorocarbon rubber (available from DAIKIN INDUSTRIES, LTD) were substituted for the additional crosslinking silicone rubber as the rubber material. Cells were seeded. Results of the UV treatment about the respective rubber plates, visibility by using the microscope, processability and results of observation using the microscope of a culture state are shown in Table 1 as below.

TABLE 1

| | | Elastic Body | UV Treatment | Visibility | Processability | 2-day Culture | 6-day Culture |
|---|---|---|---|---|---|---|---|
| Example | Silicone Rubber | LSR7005 | Excellent | Excellent | Excellent | Excellent | Excellent |
| | | LSR7030 | Excellent | Excellent | Excellent | Excellent | Excellent |
| | | LSR7060 | Excellent | Excellent | Excellent | Excellent | Excellent |
| | | LSR7070 | Excellent | Excellent | Excellent | Excellent | Excellent |
| | | LSR7080 | Excellent | Excellent | Excellent | Excellent | Excellent |
| | | LSR7090 | Excellent | Excellent | Excellent | Excellent | Excellent |
| | | LSR7030 Wet Silica 10 phr | Excellent | Excellent | Excellent | Excellent | Excellent |
| | | LSR7030 Dry Silica 10 phr | Excellent | Excellent | Excellent | Excellent | Excellent |
| Comparative Example | EPDM | Ethylene 45% | Excellent | Excellent | Bad | Excellent | Excellent |
| | | Ethylene 56% | Excellent | Excellent | Bad | Excellent | Excellent |
| | | Ethylene 61% | Excellent | Excellent | Bad | Excellent | Excellent |
| | | Ethylene 56% Wet Silica 30 phr | Excellent | Excellent | Bad | Bad | Bad |
| | | Ethylene 56% Dry Silica 30 phr | Excellent | Good | Bad | Excellent | Excellent |
| | Fluorocarbon Rubber | Without Secondary Vulcanization | Yellowness | Good | Bad | Excellent | Excellent |
| | | With Secondary Vulcanization | Yellowness | Good | Bad | Excellent | Excellent |

As clarified from Table 1, it was confirmed that the elastic bodies made of EPDM, the fluorocarbon rubber or the additional crosslinking silicone rubber had the excellent visibility, and the cells could be cultured on the elastic bodies.

(Comparative Example 2)

Although cells were seeded onto a rubber plate of an organic peroxide type silicone rubber (available from Momentive Performance Materials Inc.; TSE221-5U) as the elastic body in the same manner as Example 1, the cells could not be cultured.

INDUSTRIAL APPLICABILITY

The cell-holding container of the present invention is useful for forming the cell clusters, for the cell culture, for the observation and for the examination of the various cells exemplified by the adherent cells and the suspended cells such as the induced pluripotent stem cells and the embryonic stem cells. A cell culture system and the cell culture method using the cell-holding container are useful for culturing the suspended cells or the adherent cells, and used in the maintenance culture and the subculture of these cells.

EXPLANATIONS OF LETTERS OR NUMERALS

Numerals mean as follows. 1: cell-holding container, 2: side wall member, 3: flow path, 4: culturing chamber, 5: injection hole, 6: drain hole, 7: supporting member, 8: groove, 20, 20a, 20b, 20c: elastic body, 21: cell contacting face, 22: cell non-contacting face, 23: hard portion, 24, 24$a_1$, 24$a_2$, 24$a_3$, 24$a_4$: soft portion, 25: dented part, 26: hard frame, 27, 27$a_1$, 27$a_2$, 27$a_3$, 27$a_4$: thin portion, 28: thick portion, 29: opening part, 30: deforming means, 31: concave-convex shape, 33: aspiration-insufflation hole, 35: dented part, 90: cells, $P_1$: external force

What is claimed is:

1. A cell-holding container comprising:
   a body configured to hold cells selected from the group consisting of adherent cells and suspended cells, the adherent cells being at least one selected from the group consisting of stem cells, progenitor cells, somatic cells and germ cells, and the suspended cells being at least one selected from the group consisting of blood cells, T cells and B cells; and
   the body formed from a rubber material comprising an addition-crosslinked silicone rubber and being configured to hold the cells; and
   the body comprising plural elastic portions, the elastic portions being elastic in a direction normal to a major plane of the body, and plural non-elastic portions, the non-elastic portions being non-elastic in the direction normal to the major plane of the body, wherein the plural elastic portions and the plural non-elastic portions are integral in a single planar piece of the body.

2. The cell-holding container according to claim 1, wherein the stem cells are induced pluripotent stem cells or embryonic stem cells.

3. The cell-holding container according to claim 1, wherein the cell-holding container is configured for use in cell culture.

4. The cell-holding container according to claim 1, wherein the rubber material comprises filler selected from the group consisting of dry silica powder and/or wet silica powder.

5. The cell-holding container according to claim 1, wherein the rubber material comprises 5 to 40 parts by mass of filler selected from the group consisting of dry silica powder and/or wet silica powder relative to 100 parts by mass of the entire rubber material.

6. The cell-holding container according to claim 1, wherein the body is transparent.

7. The cell-holding container according to claim 1, wherein the elastic portions of the body have up to 0.1 mm thickness, up to A40/S hardness according to Shore A hardness and up to 3.5 MPa tensile strength, and the non-elastic portions of the deformable body have A50/S to A90/S hardness.

8. The cell-holding container according to claim 1, wherein a peripheral portion of the body is sandwiched between a supporting member and a side wall member.

9. The cell-holding container according to claim 1, wherein the elastic portions of the body are reversibly deformable from a planar shape to a concave shape or a convex shape upon application of an external force.

10. The cell-holding container according to claim 1, wherein the non-elastic portions are provided in the body in the form of squares or grids.

11. The cell-holding container according to claim 10, wherein the elastic portions have up to 0.1 mm thickness.

12. The cell-holding container according to claim 1, wherein the cell-holding container is an open-system cell-holding container.

13. The cell-holding container according to claim 1, wherein the rubber material further comprises at least one selected from the group consisting of an ethylene-propylene-diene rubber, a fluorocarbon rubber, a crosslinked silicone rubber and a fluorocarbon elastomer.

14. A cell culture method using the cell-holding container according to claim 1, comprising
introducing a cell suspension into the cell-holding container, the cell suspension comprising cells selected from the group consisting of stem cells, progenitor cells, somatic cells, germ cells, blood cells, T cells, and B cells;
deforming the elastic portions of the body of the cell-holding container from a planar shape to a concave shape after introducing the cell suspension to seed the cells into one or more concave parts of the cell-holding container;
aggregating the cells in the one or more concave parts of the cell-holding container to form cell clusters; and
deforming the elastic portions of the body from the concave shape to the planar shape after seeding the cells into the one or more concave parts and forming the cell clusters.

* * * * *